US010166069B2

United States Patent
Tran et al.

(10) Patent No.: US 10,166,069 B2
(45) Date of Patent: Jan. 1, 2019

(54) NEUROMODULATION CATHETERS HAVING JACKETED NEUROMODULATION ELEMENTS AND RELATED DEVICES, SYSTEMS, AND METHODS

(71) Applicant: Medtronic Ardian Luxembourg S.a.r.l., Luxembourg (LU)

(72) Inventors: Don Tran, Novato, CA (US); Rudy Beasley, Rohnert Park, CA (US); Jaime Rios, Santa Rosa, CA (US); Sukyoung Shin, Santa Rosa, CA (US); Sina Som, Santa Rosa, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 865 days.

(21) Appl. No.: 14/606,821

(22) Filed: Jan. 27, 2015

(65) Prior Publication Data
US 2015/0209104 A1    Jul. 30, 2015

Related U.S. Application Data

(60) Provisional application No. 61/932,224, filed on Jan. 27, 2014.

(51) Int. Cl.
*A61B 18/18* (2006.01)
*A61B 18/14* (2006.01)
(Continued)

(52) U.S. Cl.
CPC ............ *A61B 18/1492* (2013.01); *A61N 1/28* (2013.01); *A61N 1/36117* (2013.01);
(Continued)

(58) Field of Classification Search
CPC .. A61N 1/28; A61N 1/36117; A61B 18/1492; A61B 2018/00166;
(Continued)

(56) References Cited

U.S. PATENT DOCUMENTS 4,602,624 A    7/1986 Naples et al.
4,649,936 A    3/1987 Ungar et al.
(Continued)

FOREIGN PATENT DOCUMENTS

CN    2782017    5/2006
CN    201375561    1/2010
(Continued)

OTHER PUBLICATIONS

U.S. Appl. No. 95/002,110, filed Aug. 29, 2012, Demarais et al.
(Continued)

*Primary Examiner* — Lindsey G Wehrheim
(74) *Attorney, Agent, or Firm* — Shumaker & Sieffert, P.A.

(57) ABSTRACT

A neuromodulation catheter in accordance with a particular embodiment includes an elongate shaft and a neuromodulation element operably connected to the shaft. The shaft includes a proximal hypotube segment at its proximal end portion and a jacket disposed around at least a portion of an outer surface of the hypotube segment. The jacket may be made at least partially of a polymer blend including polyether block amide and polysiloxane. The neuromodulation element includes a distal hypotube segment and a tubular jacket disposed around at least a portion of an outer surface of the distal hypotube segment. The jacket has reduced-diameter segments spaced apart along its longitudinal axis. The neuromodulation element further includes band electrodes respectively seated in the reduced-diameter segments and respectively forming closed loops extending circumferentially around the jacket.

27 Claims, 9 Drawing Sheets

(51) Int. Cl.
*A61N 1/28* (2006.01)
*B29C 45/00* (2006.01)
*B29C 45/14* (2006.01)
*A61N 1/36* (2006.01)
*A61B 18/00* (2006.01)
*B29L 31/00* (2006.01)

(52) U.S. Cl.
CPC .... *B29C 45/0055* (2013.01); *B29C 45/14598* (2013.01); *A61B 2018/0022* (2013.01); *A61B 2018/00166* (2013.01); *A61B 2018/00214* (2013.01); *A61B 2018/00404* (2013.01); *A61B 2018/00434* (2013.01); *A61B 2018/00505* (2013.01); *A61B 2018/00511* (2013.01); *A61B 2018/00577* (2013.01); *A61B 2018/1467* (2013.01); *B29L 2031/7542* (2013.01); *Y10T 29/49002* (2015.01)

(58) Field of Classification Search
CPC ........... A61B 2018/00214; A61B 2018/00404; A61B 2018/00434; A61B 2018/00505; A61B 2018/00511; A61B 2018/00577; A61B 2018/1467; B29C 45/0055; B29C 45/14598; Y10T 29/49002; B29L 2031/7542
See application file for complete search history.

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 4,998,923 A | 3/1991 | Samson et al. |
| 5,158,564 A | 10/1992 | Schnepp-Pesch et al. |
| 5,300,068 A | 4/1994 | Rosar et al. |
| 5,322,064 A | 6/1994 | Lundquist |
| 5,358,514 A | 10/1994 | Schulman et al. |
| 5,368,591 A | 11/1994 | Lennox et al. |
| 5,368,592 A | 11/1994 | Stern et al. |
| 5,399,164 A | 3/1995 | Snoke et al. |
| 5,423,744 A | 6/1995 | Gencheff et al. |
| 5,441,483 A | 8/1995 | Avitall |
| 5,445,148 A | 8/1995 | Jaraczewski et al. |
| 5,454,788 A | 10/1995 | Walker et al. |
| 5,477,856 A | 12/1995 | Lundquist |
| 5,484,400 A | 1/1996 | Edwards et al. |
| 5,545,200 A | 8/1996 | West et al. |
| 5,554,114 A | 9/1996 | Wallace et al. |
| 5,558,643 A | 9/1996 | Samson et al. |
| 5,571,147 A | 11/1996 | Sluijter et al. |
| 5,582,609 A | 12/1996 | Swanson et al. |
| 5,588,964 A | 12/1996 | Imran et al. |
| 5,599,345 A | 2/1997 | Edwards et al. |
| 5,626,576 A | 5/1997 | Janssen |
| 5,628,775 A | 5/1997 | Jackson et al. |
| 5,672,174 A | 9/1997 | Gough et al. |
| 5,688,266 A | 11/1997 | Edwards et al. |
| 5,695,506 A | 12/1997 | Pike et al. |
| 5,697,928 A | 12/1997 | Walcott et al. |
| 5,700,282 A | 12/1997 | Zabara |
| 5,707,400 A | 1/1998 | Terry, Jr. et al. |
| 5,709,874 A | 1/1998 | Hanson et al. |
| 5,741,429 A | 4/1998 | Donadio, III et al. |
| 5,743,903 A | 4/1998 | Stern et al. |
| 5,772,590 A | 6/1998 | Webster, Jr. |
| 5,807,249 A | 9/1998 | Qin et al. |
| 5,823,955 A | 10/1998 | Kuck et al. |
| 5,827,272 A | 10/1998 | Breining et al. |
| 5,860,974 A | 1/1999 | Abele |
| 5,865,787 A | 2/1999 | Shapland et al. |
| 5,871,444 A | 2/1999 | Ouchi |
| 5,891,114 A | 4/1999 | Chien et al. |
| 5,893,885 A | 4/1999 | Webster et al. |
| 5,895,378 A | 4/1999 | Berenstein et al. |
| 5,904,667 A | 5/1999 | Falwell |
| 5,916,214 A | 6/1999 | Cosio et al. |
| 5,931,830 A | 8/1999 | Jacobsen et al. |
| 5,935,102 A | 8/1999 | Bowden et al. |
| 5,935,124 A | 8/1999 | Klumb et al. |
| 5,944,710 A | 8/1999 | Dev et al. |
| 5,951,539 A | 9/1999 | Nita et al. |
| 5,954,719 A | 9/1999 | Chen et al. |
| 5,961,511 A | 10/1999 | Mortier et al. |
| 5,967,978 A | 10/1999 | Littmann et al. |
| 5,971,975 A | 10/1999 | Mills et al. |
| 5,980,563 A | 11/1999 | Tu et al. |
| 5,983,141 A | 11/1999 | Sluijter et al. |
| 5,987,344 A | 11/1999 | West |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,048,338 A | 4/2000 | Larson et al. |
| 6,066,134 A | 5/2000 | Eggers et al. |
| 6,079,414 A | 6/2000 | Roth |
| 6,080,171 A | 6/2000 | Keith et al. |
| 6,090,104 A | 7/2000 | Webster, Jr. |
| 6,091,995 A | 7/2000 | Ingle et al. |
| 6,099,524 A | 8/2000 | Lipson et al. |
| 6,102,890 A | 8/2000 | Stivland et al. |
| 6,110,187 A | 8/2000 | Donlon |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,159,187 A | 12/2000 | Park et al. |
| 6,161,048 A | 12/2000 | Sluijter et al. |
| 6,165,163 A | 12/2000 | Chien et al. |
| 6,210,362 B1 | 4/2001 | Ponzi |
| 6,210,406 B1 | 4/2001 | Webster |
| 6,219,577 B1 | 4/2001 | Brown, III et al. |
| 6,224,592 B1 | 5/2001 | Eggers et al. |
| 6,245,020 B1 | 6/2001 | Moore et al. |
| 6,245,045 B1 | 6/2001 | Stratienko |
| 6,246,912 B1 | 6/2001 | Sluijter et al. |
| 6,246,914 B1 | 6/2001 | de la Rama et al. |
| 6,254,588 B1 | 7/2001 | Jones et al. |
| 6,263,224 B1 | 7/2001 | West |
| 6,273,876 B1 | 8/2001 | Klima et al. |
| 6,273,886 B1 | 8/2001 | Edwards et al. |
| 6,283,951 B1 | 9/2001 | Flaherty et al. |
| 6,283,960 B1 | 9/2001 | Ashley |
| 6,287,301 B1 | 9/2001 | Thompson et al. |
| 6,292,695 B1 | 9/2001 | Webster, Jr. et al. |
| 6,293,943 B1 | 9/2001 | Panescu et al. |
| 6,298,256 B1 | 10/2001 | Meyer |
| 6,299,623 B1 | 10/2001 | Wulfman |
| 6,314,325 B1 | 11/2001 | Fitz |
| 6,322,558 B1 | 11/2001 | Taylor et al. |
| 6,322,559 B1 | 11/2001 | Daulton et al. |
| 6,346,074 B1 | 2/2002 | Roth |
| 6,371,965 B2 | 4/2002 | Gifford, III et al. |
| 6,387,105 B1 | 5/2002 | Gifford, III et al. |
| 6,401,720 B1 | 6/2002 | Stevens et al. |
| 6,405,732 B1 | 6/2002 | Edwards et al. |
| 6,413,255 B1 | 7/2002 | Stern |
| 6,427,089 B1 | 7/2002 | Knowlton |
| 6,443,965 B1 | 9/2002 | Gifford, III et al. |
| 6,451,034 B1 | 9/2002 | Gifford, III et al. |
| 6,454,775 B1 | 9/2002 | Demarais et al. |
| 6,482,202 B1 | 11/2002 | Goble et al. |
| 6,488,679 B1 | 12/2002 | Swanson et al. |
| 6,491,705 B2 | 12/2002 | Gifford, III et al. |
| 6,497,711 B1 | 12/2002 | Plaia et al. |
| 6,500,172 B1 | 12/2002 | Panescu et al. |
| 6,506,189 B1 | 1/2003 | Rittman, III et al. |
| 6,508,804 B2 | 1/2003 | Sarge et al. |
| 6,514,226 B1 | 2/2003 | Levin et al. |
| 6,514,236 B1 | 2/2003 | Stratienko |
| 6,517,572 B2 | 2/2003 | Kugler et al. |

(56) References Cited

U.S. PATENT DOCUMENTS

| | | |
|---|---|---|
| 6,522,926 B1 | 2/2003 | Kieval et al. |
| 6,542,781 B1 | 4/2003 | Koblish et al. |
| 6,549,800 B1 | 4/2003 | Atalar et al. |
| 6,562,034 B2 | 5/2003 | Edwards et al. |
| 6,565,582 B2 | 5/2003 | Gifford, III et al. |
| 6,569,177 B1 | 5/2003 | Dillard et al. |
| 6,585,718 B2 | 7/2003 | Hayzelden et al. |
| 6,610,046 B1 | 8/2003 | Usami et al. |
| 6,611,720 B2 | 8/2003 | Hata et al. |
| 6,613,046 B1 | 9/2003 | Jenkins et al. |
| 6,616,624 B1 | 9/2003 | Kieval |
| 6,622,731 B2 | 9/2003 | Daniel et al. |
| 6,628,976 B1 | 9/2003 | Fuimaono et al. |
| 6,632,193 B1 | 10/2003 | Davison et al. |
| 6,635,054 B2 | 10/2003 | Fjield et al. |
| 6,640,120 B1 | 10/2003 | Swanson et al. |
| 6,648,854 B1 | 11/2003 | Patterson et al. |
| 6,651,672 B2 | 11/2003 | Roth |
| 6,656,195 B2 | 12/2003 | Peters et al. |
| 6,659,981 B2 | 12/2003 | Stewart et al. |
| 6,669,670 B1 | 12/2003 | Muni et al. |
| 6,669,692 B1 | 12/2003 | Nelson et al. |
| 6,676,678 B2 | 1/2004 | Gifford, III et al. |
| 6,679,268 B2 | 1/2004 | Stevens et al. |
| 6,682,541 B1 | 1/2004 | Gifford, III et al. |
| 6,685,648 B2 | 2/2004 | Flaherty et al. |
| 6,695,857 B2 | 2/2004 | Gifford, III et al. |
| 6,699,257 B2 | 3/2004 | Gifford, III et al. |
| 6,702,811 B2 | 3/2004 | Stewart et al. |
| 6,706,010 B1 | 3/2004 | Miki et al. |
| 6,711,444 B2 | 3/2004 | Koblish |
| 6,716,207 B2 | 4/2004 | Farnholtz |
| 6,723,043 B2 | 4/2004 | Kleeman et al. |
| 6,736,835 B2 | 5/2004 | Pellegrino et al. |
| 6,745,080 B2 | 6/2004 | Koblish |
| 6,749,560 B1 | 6/2004 | Konstorum et al. |
| 6,752,805 B2 | 6/2004 | Maguire et al. |
| 6,770,070 B1 | 8/2004 | Balbierz |
| 6,790,206 B2 | 9/2004 | Panescu |
| 6,817,999 B2 | 11/2004 | Berube et al. |
| 6,829,497 B2 | 12/2004 | Mogul |
| 6,830,568 B1 | 12/2004 | Kesten et al. |
| 6,845,267 B2 | 1/2005 | Harrison et al. |
| 6,849,075 B2 | 2/2005 | Bertolero et al. |
| 6,850,801 B2 | 2/2005 | Kieval et al. |
| 6,869,431 B2 | 3/2005 | Maguire et al. |
| 6,884,260 B2 | 4/2005 | Kugler et al. |
| 6,885,888 B2 | 4/2005 | Rezai |
| 6,889,694 B2 | 5/2005 | Hooven |
| 6,890,329 B2 | 5/2005 | Carroll et al. |
| 6,893,436 B2 | 5/2005 | Woodard et al. |
| 6,909,009 B2 | 6/2005 | Koridze |
| 6,915,806 B2 | 7/2005 | Pacek et al. |
| 6,917,834 B2 | 7/2005 | Koblish et al. |
| 6,923,808 B2 | 8/2005 | Taimisto |
| 6,926,669 B1 | 8/2005 | Stewart et al. |
| 6,926,713 B2 | 8/2005 | Rioux et al. |
| 6,939,346 B2 | 9/2005 | Kannenberg et al. |
| 6,945,956 B2 | 9/2005 | Waldhauser et al. |
| 6,949,097 B2 | 9/2005 | Stewart et al. |
| 6,955,175 B2 | 10/2005 | Stevens et al. |
| 6,966,908 B2 | 11/2005 | Maguire et al. |
| 6,984,238 B2 | 1/2006 | Gifford, III et al. |
| 7,058,456 B2 | 6/2006 | Pierce |
| 7,087,051 B2 | 8/2006 | Bourne et al. |
| 7,100,614 B2 | 9/2006 | Stevens et al. |
| 7,102,151 B2 | 9/2006 | Reinberg et al. |
| 7,110,828 B2 | 9/2006 | Kolberg et al. |
| 7,112,211 B2 | 9/2006 | Gifford, III et al. |
| 7,115,183 B2 | 10/2006 | Larson et al. |
| 7,137,990 B2 | 11/2006 | Hebert et al. |
| 7,149,574 B2 | 12/2006 | Yun et al. |
| 7,153,315 B2 | 12/2006 | Miller |
| 7,162,303 B2 | 1/2007 | Levin et al. |
| 7,172,610 B2 | 2/2007 | Heitzmann et al. |
| 7,184,811 B2 | 2/2007 | Phan et al. |
| 7,192,427 B2 | 3/2007 | Chapelon et al. |
| 7,221,979 B2 | 5/2007 | Zhou et al. |
| 7,238,184 B2 | 7/2007 | Megerman et al. |
| 7,241,273 B2 | 7/2007 | Maguire et al. |
| 7,276,062 B2 | 10/2007 | McDaniel et al. |
| 7,294,127 B2 | 11/2007 | Leung et al. |
| 7,311,705 B2 | 12/2007 | Sra |
| 7,338,467 B2 | 3/2008 | Lutter |
| 7,367,972 B2 | 5/2008 | Francischelli et al. |
| 7,381,200 B2 | 6/2008 | Katoh et al. |
| 7,390,894 B2 | 6/2008 | Weinshilboum et al. |
| 7,393,338 B2 | 7/2008 | Nita |
| 7,402,151 B2 | 7/2008 | Rosenman et al. |
| 7,486,805 B2 | 2/2009 | Krattiger |
| 7,488,338 B2 | 2/2009 | Eidenschink |
| 7,494,486 B2 | 2/2009 | Mische et al. |
| 7,494,488 B2 | 2/2009 | Weber et al. |
| 7,497,858 B2 | 3/2009 | Chapelon et al. |
| 7,517,349 B2 | 4/2009 | Truckai et al. |
| 7,520,863 B2 | 4/2009 | Grewe et al. |
| 7,540,865 B2 | 6/2009 | Griffin et al. |
| 7,563,247 B2 | 7/2009 | Maguire et al. |
| 7,617,005 B2 | 11/2009 | Demarais et al. |
| 7,620,451 B2 | 11/2009 | Demarais et al. |
| 7,637,903 B2 | 12/2009 | Lentz et al. |
| 7,647,115 B2 | 1/2010 | Levin et al. |
| 7,653,438 B2 | 1/2010 | Deem et al. |
| 7,682,319 B2 | 3/2010 | Martin et al. |
| 7,699,809 B2 | 4/2010 | Urmey |
| 7,706,894 B2 | 4/2010 | Stewart et al. |
| 7,708,704 B2 | 5/2010 | Mitelberg et al. |
| 7,717,853 B2 | 5/2010 | Nita |
| 7,717,948 B2 | 5/2010 | Demarais et al. |
| 7,727,187 B2 | 6/2010 | Lentz |
| 7,758,520 B2 | 7/2010 | Griffin et al. |
| 7,763,012 B2 | 7/2010 | Petrick et al. |
| 7,771,410 B2 | 8/2010 | Venturelli |
| 7,771,421 B2 | 8/2010 | Stewart et al. |
| 7,778,703 B2 | 8/2010 | Gross et al. |
| 7,780,660 B2 | 8/2010 | Bourne et al. |
| 7,785,289 B2 | 8/2010 | Rios et al. |
| 7,806,871 B2 | 10/2010 | Li et al. |
| 7,811,265 B2 | 10/2010 | Hering et al. |
| 7,811,281 B1 | 10/2010 | Rentrop |
| 7,815,637 B2 | 10/2010 | Ormsby et al. |
| 7,819,866 B2 | 10/2010 | Bednarek |
| 7,846,157 B2 | 12/2010 | Kozel |
| 7,850,685 B2 | 12/2010 | Kunis et al. |
| 7,862,565 B2 | 1/2011 | Eder et al. |
| 7,863,897 B2 | 1/2011 | Slocum, Jr. et al. |
| 7,896,873 B2 | 3/2011 | Hiller et al. |
| 7,905,862 B2 | 3/2011 | Sampson |
| 7,938,830 B2 | 5/2011 | Saadat et al. |
| 7,967,816 B2 | 6/2011 | Ocel et al. |
| 7,989,042 B2 | 8/2011 | Obara et al. |
| 8,007,440 B2 | 8/2011 | Magnin et al. |
| 8,007,462 B2 | 8/2011 | Gibson et al. |
| 8,027,718 B2 | 9/2011 | Spinner et al. |
| 8,043,288 B2 | 10/2011 | Dando et al. |
| 8,075,580 B2 | 12/2011 | Makower |
| 8,088,127 B2 | 1/2012 | Mayse et al. |
| 8,092,444 B2 | 1/2012 | Lentz et al. |
| 8,124,876 B2 | 2/2012 | Dayton et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,172,829 B2 | 5/2012 | Farnholtz |
| 8,175,711 B2 | 5/2012 | Demarais et al. |
| 8,190,238 B2 | 5/2012 | Moll et al. |
| 8,241,217 B2 | 8/2012 | Chiang et al. |
| 8,251,977 B2 | 8/2012 | Partlett |
| 8,292,881 B2 | 10/2012 | Brannan et al. |
| 8,343,145 B2 | 1/2013 | Brannan |

(56) References Cited

U.S. PATENT DOCUMENTS

| | | | |
|---|---|---|---|
| 8,366,615 B2 * | 2/2013 | Razavi | A61B 5/042 600/371 |
| 8,376,865 B2 | 2/2013 | Forster et al. | |
| 8,388,680 B2 | 3/2013 | Starksen et al. | |
| 8,398,629 B2 | 3/2013 | Thistle | |
| 8,401,650 B2 | 3/2013 | Simon et al. | |
| 8,409,193 B2 | 4/2013 | Young et al. | |
| 8,409,195 B2 | 4/2013 | Young | |
| 8,418,362 B2 | 4/2013 | Zerfas et al. | |
| 8,473,023 B2 | 6/2013 | Worley et al. | |
| 8,485,992 B2 | 7/2013 | Griffin et al. | |
| 8,486,060 B2 | 7/2013 | Kotmel et al. | |
| 8,486,063 B2 | 7/2013 | Werneth et al. | |
| 8,740,849 B1 | 6/2014 | Fischell et al. | |
| 8,974,451 B2 | 3/2015 | Smith | |
| 9,162,046 B2 | 10/2015 | Hill et al. | |
| 2002/0022864 A1 | 2/2002 | Mahvi et al. | |
| 2002/0062123 A1 | 5/2002 | McClurken et al. | |
| 2002/0087208 A1 | 7/2002 | Koblish et al. | |
| 2002/0107515 A1 | 8/2002 | Edwards et al. | |
| 2002/0139379 A1 | 10/2002 | Edwards et al. | |
| 2002/0165532 A1 | 11/2002 | Hill et al. | |
| 2002/0183682 A1 | 12/2002 | Darvish et al. | |
| 2003/0004510 A1 | 1/2003 | Wham et al. | |
| 2003/0050635 A1 | 3/2003 | Truckai et al. | |
| 2003/0050681 A1 | 3/2003 | Pianca et al. | |
| 2003/0060858 A1 | 3/2003 | Kieval et al. | |
| 2003/0065317 A1 | 4/2003 | Rudie et al. | |
| 2003/0074039 A1 | 4/2003 | Puskas | |
| 2003/0092995 A1 | 5/2003 | Thompson | |
| 2003/0125790 A1 | 7/2003 | Fastovsky et al. | |
| 2003/0139689 A1 | 7/2003 | Shturman et al. | |
| 2003/0181897 A1 | 9/2003 | Thomas et al. | |
| 2003/0195507 A1 | 10/2003 | Stewart et al. | |
| 2003/0199863 A1 | 10/2003 | Swanson et al. | |
| 2003/0216792 A1 | 11/2003 | Levin et al. | |
| 2003/0220639 A1 | 11/2003 | Chapelon et al. | |
| 2003/0229340 A1 | 12/2003 | Sherry et al. | |
| 2003/0233099 A1 | 12/2003 | Danaek et al. | |
| 2004/0006359 A1 | 1/2004 | Laguna | |
| 2004/0010289 A1 | 1/2004 | Biggs et al. | |
| 2004/0030375 A1 * | 2/2004 | Pierce | A61B 17/221 607/125 |
| 2004/0073206 A1 | 4/2004 | Foley et al. | |
| 2004/0088002 A1 | 5/2004 | Boyle et al. | |
| 2004/0167509 A1 | 8/2004 | Taimisto | |
| 2004/0215186 A1 | 10/2004 | Cornelius et al. | |
| 2005/0004515 A1 | 1/2005 | Hart et al. | |
| 2005/0010095 A1 | 1/2005 | Stewart et al. | |
| 2005/0080409 A1 | 4/2005 | Young et al. | |
| 2005/0096647 A1 | 5/2005 | Steinke et al. | |
| 2005/0187579 A1 | 8/2005 | Danek et al. | |
| 2005/0228286 A1 | 10/2005 | Messerly et al. | |
| 2005/0228460 A1 | 10/2005 | Levin et al. | |
| 2005/0273006 A1 | 12/2005 | Stewart et al. | |
| 2006/0004323 A1 | 1/2006 | Chang et al. | |
| 2006/0004346 A1 | 1/2006 | Begg | |
| 2006/0025765 A1 | 2/2006 | Landman et al. | |
| 2006/0074403 A1 | 4/2006 | Rafiee | |
| 2006/0085054 A1 | 4/2006 | Zikorus et al. | |
| 2006/0089637 A1 | 4/2006 | Werneth et al. | |
| 2006/0095029 A1 | 5/2006 | Young et al. | |
| 2006/0122587 A1 | 6/2006 | Sharareh | |
| 2006/0142753 A1 | 6/2006 | Francischelli et al. | |
| 2006/0167498 A1 | 7/2006 | DiLorenzo | |
| 2006/0184221 A1 | 8/2006 | Stewart et al. | |
| 2006/0206150 A1 | 9/2006 | Demarais et al. | |
| 2006/0212076 A1 | 9/2006 | Demarais et al. | |
| 2006/0224153 A1 | 10/2006 | Fischell et al. | |
| 2006/0263393 A1 | 11/2006 | Demopulos et al. | |
| 2006/0271111 A1 | 11/2006 | Demarais et al. | |
| 2006/0276846 A1 | 12/2006 | Malecki et al. | |
| 2006/0287644 A1 | 12/2006 | Inganas et al. | |
| 2007/0027390 A1 | 2/2007 | Maschke et al. | |
| 2007/0049924 A1 | 3/2007 | Rahn | |
| 2007/0067008 A1 | 3/2007 | Scheiner et al. | |
| 2007/0073151 A1 | 3/2007 | Lee | |
| 2007/0100405 A1 | 5/2007 | Thompson et al. | |
| 2007/0106247 A1 | 5/2007 | Burnett et al. | |
| 2007/0112327 A1 | 5/2007 | Yun et al. | |
| 2007/0129720 A1 | 6/2007 | Demarais et al. | |
| 2007/0149963 A1 | 6/2007 | Matsukuma et al. | |
| 2007/0156114 A1 | 7/2007 | Worley et al. | |
| 2007/0179496 A1 | 8/2007 | Swoyer et al. | |
| 2007/0197891 A1 | 8/2007 | Shachar et al. | |
| 2007/0265687 A1 | 11/2007 | Deem et al. | |
| 2007/0270779 A1 | 11/2007 | Jacobs et al. | |
| 2008/0004658 A1 | 1/2008 | Malecki et al. | |
| 2008/0015562 A1 | 1/2008 | Hong et al. | |
| 2008/0071269 A1 | 3/2008 | Hilario et al. | |
| 2008/0077119 A1 | 3/2008 | Snyder et al. | |
| 2008/0086047 A1 | 4/2008 | McDaniel et al. | |
| 2008/0091193 A1 | 4/2008 | Kauphusman et al. | |
| 2008/0108867 A1 | 5/2008 | Zhou | |
| 2008/0140072 A1 | 6/2008 | Stangenes et al. | |
| 2008/0177205 A1 | 7/2008 | Rama et al. | |
| 2008/0287918 A1 | 11/2008 | Rosenman et al. | |
| 2008/0319513 A1 | 12/2008 | Pu et al. | |
| 2009/0012465 A1 | 1/2009 | Latini | |
| 2009/0030312 A1 | 1/2009 | Hadjicostis | |
| 2009/0036948 A1 | 2/2009 | Levin et al. | |
| 2009/0043372 A1 | 2/2009 | Northrop et al. | |
| 2009/0069671 A1 | 3/2009 | Anderson | |
| 2009/0118620 A1 | 5/2009 | Tgavalekos et al. | |
| 2009/0149848 A1 | 6/2009 | Werneth et al. | |
| 2009/0157048 A1 | 6/2009 | Sutermeister et al. | |
| 2009/0163850 A1 | 6/2009 | Betts et al. | |
| 2009/0171333 A1 | 7/2009 | Hon | |
| 2009/0221955 A1 | 9/2009 | Babaev | |
| 2009/0306650 A1 | 12/2009 | Govari et al. | |
| 2009/0312606 A1 | 12/2009 | Dayton et al. | |
| 2010/0030061 A1 | 2/2010 | Canfield et al. | |
| 2010/0069882 A1 | 3/2010 | Jennings et al. | |
| 2010/0137860 A1 | 6/2010 | Demarais et al. | |
| 2010/0137952 A1 | 6/2010 | Demarais et al. | |
| 2010/0168740 A1 | 7/2010 | Stewart et al. | |
| 2010/0179512 A1 | 7/2010 | Chong et al. | |
| 2010/0191112 A1 | 7/2010 | Demarais et al. | |
| 2010/0217184 A1 | 8/2010 | Koblish et al. | |
| 2010/0222851 A1 | 9/2010 | Deem et al. | |
| 2010/0222854 A1 | 9/2010 | Demarais et al. | |
| 2010/0249604 A1 | 9/2010 | Hastings et al. | |
| 2010/0312141 A1 | 12/2010 | Keast et al. | |
| 2010/0324482 A1 | 12/2010 | Farnholtz | |
| 2011/0021976 A1 | 1/2011 | Li et al. | |
| 2011/0028962 A1 | 2/2011 | Werneth et al. | |
| 2011/0034989 A1 | 2/2011 | Al-Marashi et al. | |
| 2011/0054464 A1 | 3/2011 | Werneth et al. | |
| 2011/0054465 A1 | 3/2011 | Werneth et al. | |
| 2011/0071400 A1 | 3/2011 | Hastings et al. | |
| 2011/0071401 A1 | 3/2011 | Hastings et al. | |
| 2011/0112476 A1 | 5/2011 | Kauphusman et al. | |
| 2011/0270173 A1 | 11/2011 | Gibson et al. | |
| 2012/0059241 A1 | 3/2012 | Hastings et al. | |
| 2012/0130289 A1 | 5/2012 | Demarais et al. | |
| 2012/0130345 A1 | 5/2012 | Levin et al. | |
| 2012/0172837 A1 | 7/2012 | Demarais et al. | |
| 2012/0197246 A1 | 8/2012 | Mauch | |
| 2012/0265066 A1 | 10/2012 | Crow et al. | |
| 2013/0035681 A1 | 2/2013 | Subramaniam et al. | |
| 2013/0090647 A1 | 4/2013 | Smith | |
| 2013/0090649 A1 | 4/2013 | Smith et al. | |
| 2013/0090651 A1 | 4/2013 | Smith | |
| 2013/0090652 A1 | 4/2013 | Jenson | |
| 2013/0096550 A1 | 4/2013 | Hill | |
| 2013/0096553 A1 | 4/2013 | Hill et al. | |
| 2013/0096554 A1 | 4/2013 | Groff et al. | |
| 2013/0123770 A1 | 5/2013 | Smith | |
| 2013/0131667 A1 | 5/2013 | Jenson et al. | |
| 2013/0150808 A1 | 6/2013 | Ogle et al. | |
| 2013/0172879 A1 | 7/2013 | Sutermeister et al. | |
| 2013/0172881 A1 | 7/2013 | Hill et al. | |
| 2013/0184642 A1 | 7/2013 | O'Donnell et al. | |
| 2013/0184703 A1 | 7/2013 | Shireman et al. | |

(56) References Cited

U.S. PATENT DOCUMENTS

| | | |
|---|---|---|
| 2013/0237780 A1 | 9/2013 | Beasley et al. |
| 2013/0274730 A1 | 10/2013 | Anderson et al. |
| 2013/0274731 A1 | 10/2013 | Anderson et al. |
| 2013/0274737 A1 | 10/2013 | Wang et al. |
| 2013/0304061 A1 | 11/2013 | Chang et al. |
| 2014/0094787 A1 | 4/2014 | Reynolds |
| 2014/0121641 A1 | 5/2014 | Fischell et al. |
| 2014/0121644 A1 | 5/2014 | Fischell et al. |
| 2014/0135755 A1 | 5/2014 | Sutermeister et al. |
| 2014/0214026 A1 | 7/2014 | Degen |
| 2014/0249524 A1 | 9/2014 | Kocur |
| 2014/0276613 A1 | 9/2014 | Goodman et al. |
| 2014/0276752 A1 | 9/2014 | Wang et al. |
| 2014/0276787 A1 | 9/2014 | Wang et al. |
| 2014/0358079 A1 | 12/2014 | Fischell et al. |
| 2014/0378967 A1 | 12/2014 | Willard et al. |
| 2015/0265339 A1 | 9/2015 | Lindquist et al. |

FOREIGN PATENT DOCUMENTS

| | | |
|---|---|---|
| CN | 102125460 | 7/2011 |
| CN | 102125725 | 7/2011 |
| CN | 102885648 | 1/2013 |
| CN | 102885649 | 1/2013 |
| CN | 102908188 | 2/2013 |
| CN | 102908189 | 2/2013 |
| DE | 102005041601 | 4/2007 |
| DE | 102012104705 | 12/2013 |
| EP | 0348136 | 12/1989 |
| EP | 0352955 | 1/1990 |
| EP | 0512359 | 11/1992 |
| EP | 0542246 | 5/1993 |
| EP | 626818 | 12/1994 |
| EP | 0647435 | 4/1995 |
| EP | 652026 | 5/1995 |
| EP | 664990 | 8/1995 |
| EP | 0680351 | 11/1995 |
| EP | 727184 | 8/1996 |
| EP | 0787019 | 8/1997 |
| EP | 0834289 | 4/1998 |
| EP | 862478 | 9/1998 |
| EP | 0937481 | 8/1999 |
| EP | 944353 | 9/1999 |
| EP | 0951244 | 10/1999 |
| EP | 0984806 | 3/2000 |
| EP | 1286625 | 3/2003 |
| EP | 1326550 | 7/2003 |
| EP | 1374943 | 1/2004 |
| EP | 1656963 | 5/2006 |
| EP | 1709922 | 10/2006 |
| EP | 1768732 | 4/2007 |
| EP | 1787674 | 5/2007 |
| EP | 1824548 | 8/2007 |
| EP | 1827558 | 9/2007 |
| EP | 1857134 | 11/2007 |
| EP | 1906853 | 4/2008 |
| EP | 1968679 | 9/2008 |
| EP | 2027882 | 2/2009 |
| EP | 2320821 | 5/2011 |
| EP | 2340765 | 7/2011 |
| EP | 2389974 | 11/2011 |
| EP | 2398540 | 12/2011 |
| EP | 2445568 | 5/2012 |
| EP | 2747688 | 7/2014 |
| EP | 2759314 | 7/2014 |
| EP | 2804554 | 11/2014 |
| EP | 2900160 | 8/2015 |
| EP | 2900161 | 8/2015 |
| EP | 2990070 | 3/2016 |
| EP | 3010436 | 4/2016 |
| EP | 2768563 | 11/2016 |
| WO | WO-9101772 | 2/1991 |
| WO | WO-9215356 | 9/1992 |
| WO | 1994007446 | 4/1994 |
| WO | WO-9419039 | 9/1994 |
| WO | 1994028809 | 12/1994 |
| WO | WO-1995025472 | 9/1995 |
| WO | 1995031142 | 11/1995 |
| WO | WO-9729800 | 8/1997 |
| WO | WO-1997036548 | 10/1997 |
| WO | WO-9748435 | 12/1997 |
| WO | 1998042403 | 10/1998 |
| WO | WO-9843530 | 10/1998 |
| WO | WO-9848885 | 11/1998 |
| WO | WO-9850098 | 11/1998 |
| WO | WO-9852637 | 11/1998 |
| WO | 1999000060 | 1/1999 |
| WO | WO-9900060 | 1/1999 |
| WO | WO-9911313 | 3/1999 |
| WO | WO-2001022897 | 4/2001 |
| WO | 2001037723 | 5/2001 |
| WO | 2001037746 | 5/2001 |
| WO | WO-2001070114 | 9/2001 |
| WO | WO-0230310 | 4/2002 |
| WO | 2002080766 | 10/2002 |
| WO | WO-02089908 | 11/2002 |
| WO | 2003022167 | 3/2003 |
| WO | 2003082080 | 10/2003 |
| WO | WO-2005030072 | 4/2005 |
| WO | WO-2005041748 | 5/2005 |
| WO | WO-2005110528 | 11/2005 |
| WO | WO-2006/009588 | 1/2006 |
| WO | WO-2006041881 | 4/2006 |
| WO | WO-2006065949 | 6/2006 |
| WO | 2006105121 | 10/2006 |
| WO | WO-2007008954 | 1/2007 |
| WO | WO-2007059277 | 5/2007 |
| WO | 2007078997 | 7/2007 |
| WO | WO-2007117359 | 10/2007 |
| WO | 2008010150 | 1/2008 |
| WO | 2008036281 | 3/2008 |
| WO | 2008049084 | 4/2008 |
| WO | WO-2008064399 | 6/2008 |
| WO | WO-2008101244 | 8/2008 |
| WO | WO-2008139347 | 11/2008 |
| WO | 2009082635 | 7/2009 |
| WO | 2009088678 | 7/2009 |
| WO | 2009137819 | 11/2009 |
| WO | WO-2010091701 | 8/2010 |
| WO | 2010134503 | 11/2010 |
| WO | WO-2011056311 | 5/2011 |
| WO | WO-2012100095 | 7/2012 |
| WO | WO-2013016203 | 1/2013 |
| WO | WO-2013/055685 | 4/2013 |
| WO | WO-2013055537 | 4/2013 |
| WO | WO-2013055815 | 4/2013 |
| WO | WO-2013055826 | 4/2013 |
| WO | WO-2013056672 | 4/2013 |
| WO | WO-2013058962 | 4/2013 |
| WO | WO-2013106054 | 7/2013 |
| WO | WO-2013109318 | 7/2013 |
| WO | WO-2013158676 | 10/2013 |
| WO | WO-2013158678 | 10/2013 |
| WO | WO-2014012282 | 1/2014 |
| WO | WO-2014036163 | 3/2014 |
| WO | 2014174662 | 10/2014 |
| WO | 2016090175 | 6/2016 |

OTHER PUBLICATIONS

U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.

(56) References Cited

OTHER PUBLICATIONS

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards$^{TM}$" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.

(56) References Cited

OTHER PUBLICATIONS

Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).

Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Schneider, Peter A., "Endovascular Skills—Guidewire and Catheter Skills for Endovascular Surgery," Second Edition Revised and Expanded, 10 pages, (2003).
Kandarpa, Krishna et al., "Handbook of Interventional Radiologic Procedures", Third Edition, pp. 194-210 (2002).
ThermoCool Irrigated Catheter and Integrated Ablation System, Biosense Webster (2006), 6 pages.
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP2092957, Granted Jan. 5, 2011, Date of Opposition Oct. 5, 2011, 26 pages.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Oz, Mehmet, Pressure Relief, Time, Jan. 9, 2012, 2 pages. <www.time.come/time/printout/0,8816,2103278,00.html>.

(56) References Cited

OTHER PUBLICATIONS

Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Pulmonary Vein Stenosis Following Catheter Ablation of Atrial Fibrillation, Curr. Opin. Cardio. 20: 484-490, 2005.
Papademetriou, Vasilios, Renal Sympathetic Denervation for the Treatment of Difficult-to-Control or Resistant Hypertension, Int. Journal of Hypertension, 2011, 8 pages.
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.

Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):91 1-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
International Search Report and Written Opinion for International Application No. PCT/US2015/013042, dated Apr. 7, 2015, 10 pages.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Opposition to European Patent No. 2465470, Granted Oct. 28, 2015, Date of Opposition Jul. 27, 2016, 34 pp.
Pieper, et al., "Design and Implementation of a New Computerized System for Intraoperative Cardiac Mapping" Journal of Applied Physiology, 1991, vol. 71 (4), pp. 1529-1539.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.

* cited by examiner

NEUROMODULATION CATHETERS HAVING JACKETED NEUROMODULATION ELEMENTS AND RELATED DEVICES, SYSTEMS, AND METHODS

CROSS-REFERENCE TO RELATED APPLICATION(S)

This application claims the benefit of U.S. Provisional Patent Application No. 61/932,224, filed on Jan. 27, 2014, the disclosure of which is incorporated herein by reference in its entirety.

TECHNICAL FIELD

The present technology is related to catheters. In particular, at least some embodiments are related to neuromodulation catheters including neuromodulation elements configured to deliver energy to nerves at or near a treatment location within a body lumen.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS, in particular, has been identified experimentally and in humans as a likely contributor to the complex pathophysiologies of hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

In FIG. 15, the portion of the distal jacket is shown without a band electrode. In FIG. 16, the portion of the distal jacket is shown resiliently deformed inwardly as a band electrode is moved toward the reduced-diameter segment. In FIG. 17, the portion of the distal jacket is shown with the band electrode seated in the reduced-diameter segment.

DETAILED DESCRIPTION

Specific details of systems, devices, and methods in accordance with several embodiments of the present technology are disclosed herein with reference to FIGS. 1-21. Although the systems, devices, and methods may be disclosed herein primarily or entirely with respect to intravascular renal neuromodulation, other applications in addition to those disclosed herein are within the scope of the present technology. For example, systems, devices, and methods in accordance with at least some embodiments of the present technology may be useful for neuromodulation within a body lumen other than a vessel, for extravascular neuromodulation, for non-renal neuromodulation, and/or for use in therapies other than neuromodulation. Furthermore, it should understood, in general, that other systems, devices, and methods in addition to those disclosed herein are within the scope of the present technology. For example, systems, devices, and methods in accordance with embodiments of the present technology can have different and/or additional configurations, components, and procedures than those disclosed herein. Moreover, a person of ordinary skill in the art will understand that systems, devices, and methods in accordance with embodiments of the present technology can be without one or more of the configurations, components, and/or procedures disclosed herein without deviating from the present technology.

As used herein, the terms "distal" and "proximal" define a position or direction with respect to a clinician or a clinician's control device (e.g., a handle of a catheter). The terms, "distal" and "distally" refer to a position distant from or in a direction away from a clinician or a clinician's control device. The terms "proximal" and "proximally" refer to a position near or in a direction toward a clinician or a clinician's control device. The headings provided herein are for convenience only and should not be construed as limiting the subject matter disclosed.

Selected Examples of Neuromodulation Catheters and Related Systems and Devices

Figure 1:
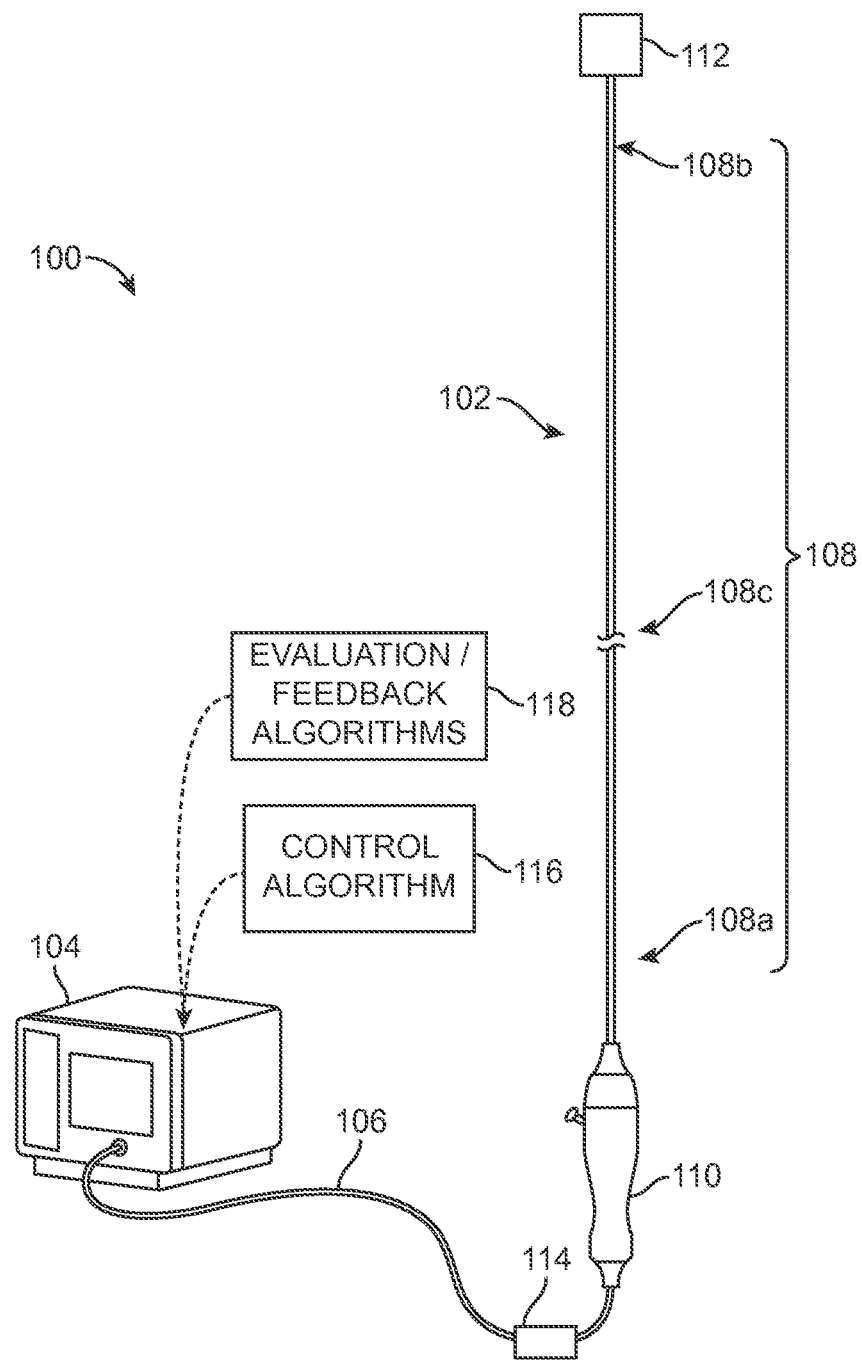
FIG. 1 is a partially schematic perspective view illustrating a therapeutic system configured in accordance with an embodiment of the present technology. The system is shown in FIG. 1 including a neuromodulation catheter having a shaft.

FIG. 1 is a partially schematic perspective view illustrating a therapeutic system 100 configured in accordance with an embodiment of the present technology. The system 100 can include a neuromodulation catheter 102, a console 104, and a cable 106 extending between the catheter 102 and the console 104. The catheter 102 can include an elongate shaft 108 having a proximal end portion 108a, a distal end portion 108b, and an intermediate portion 108c therebetween. The catheter 102 can further include a handle 110 operably connected to the shaft 108 via the proximal end portion 108a of the shaft 108 and a neuromodulation element 112 (shown schematically in FIG. 1) operably connected to the shaft 108 via the distal end portion 108b of the shaft 108. The shaft 108 can be configured to locate the neuromodulation element 112 at a treatment location within or otherwise proximate to a body lumen (e.g., a blood vessel, a duct, an airway, or another naturally occurring lumen within the human body). In some embodiments, the shaft 108 can be configured to locate the neuromodulation element 112 at an intraluminal (e.g., intravascular) location. The neuromodulation element 112 can be configured to provide or support a neuromodulation treatment at the treatment location. The shaft 108 and the neuromodulation element 112 can be 2, 3, 4, 5, 6, or 7 French or other suitable sizes.

Intraluminal delivery of the catheter 102 can include percutaneously inserting a guide wire (not shown) into a body lumen of a patient and moving the shaft 108 and the neuromodulation element 112 along the guide wire until the neuromodulation element 112 reaches a suitable treatment location. Alternatively, the catheter 102 can be a steerable or non-steerable device configured for use without a guide wire. As another alternative, the neuromodulation catheter 102 can be configured for use with a guide catheter or sheath (not shown). In the illustrated embodiment, the console 104 is configured to control, monitor, supply, and/or otherwise support operation of the catheter 102. In other embodiments, the catheter 102 can be self-contained or otherwise configured for operation independent of the console 104. When present, the console 104 can be configured to generate a selected form and/or magnitude of energy for delivery to tissue at a treatment location via the neuromodulation element 112. For example, the console 104 can be configured to generate radio frequency (RF) energy (e.g., monopolar and/or bipolar RF energy) and/or another suitable type of energy for delivery to tissue at a treatment location via electrodes (not shown) of the neuromodulation element 112. Along the cable 106 or at another suitable location within the system 100, the system 100 can include a control device 114 configured to initiate, terminate, and/or adjust operation of one or more components of the catheter 102 directly and/or via the console 104. The console 104 can be configured to execute an automated control algorithm 116 and/or to receive control instructions from an operator. Similarly, the console 104 can be configured to provide feedback to an operator before, during, and/or after a treatment procedure via an evaluation/feedback algorithm 118.

Figure 2:
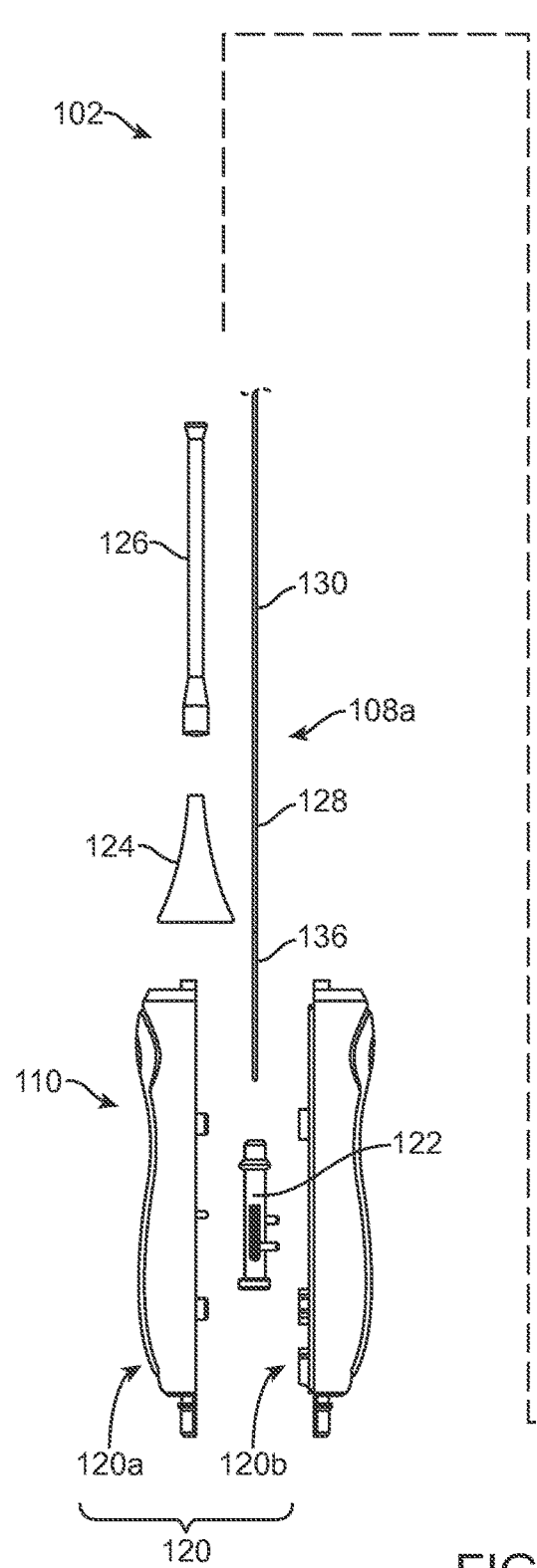
FIG. 2 is an exploded profile view of the catheter shown in FIG. 1.
Figure 2:
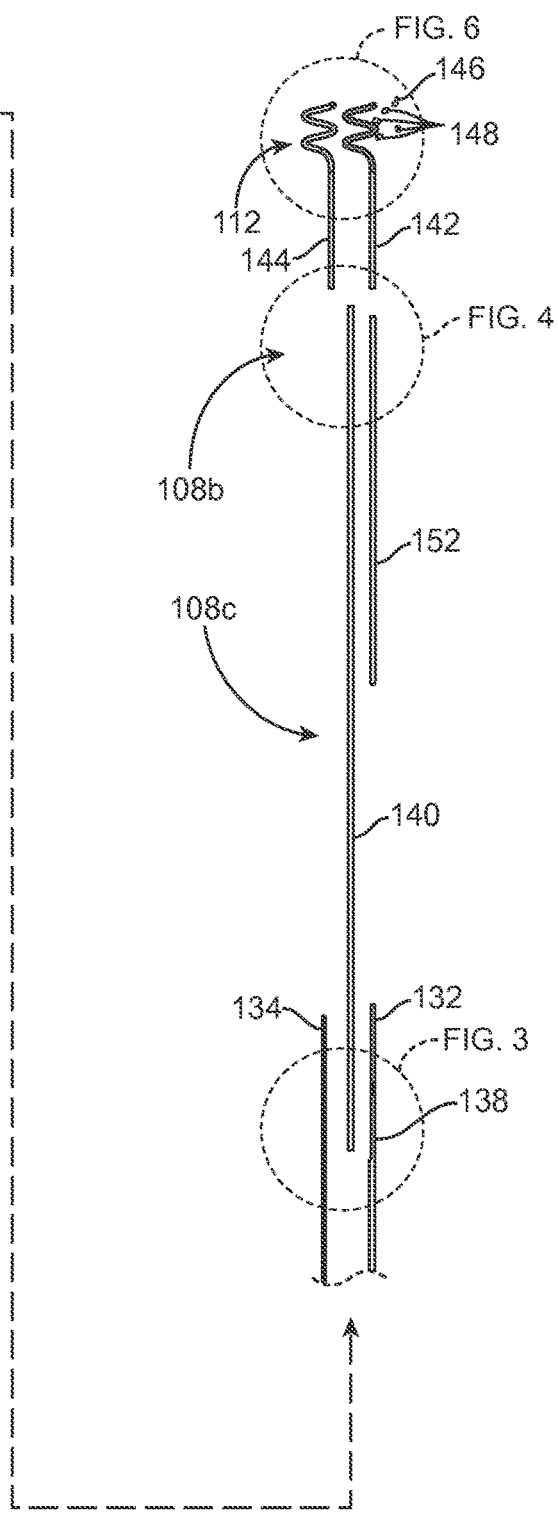
Figure 3:
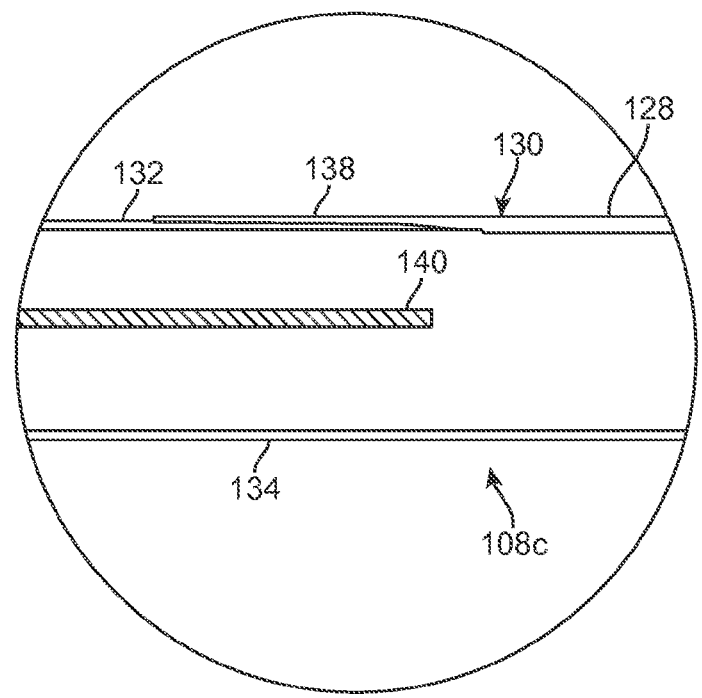
FIGS. 3, 4 and 6 are enlarged exploded profile views of portions of the catheter shown in FIG. 1 taken at respective locations designated in FIG. 2.
Figure 4:
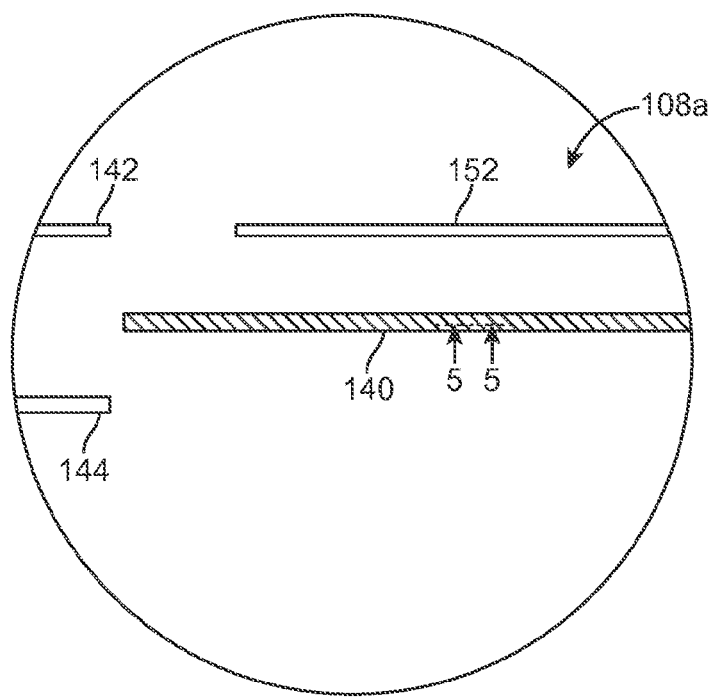
Figure 6:
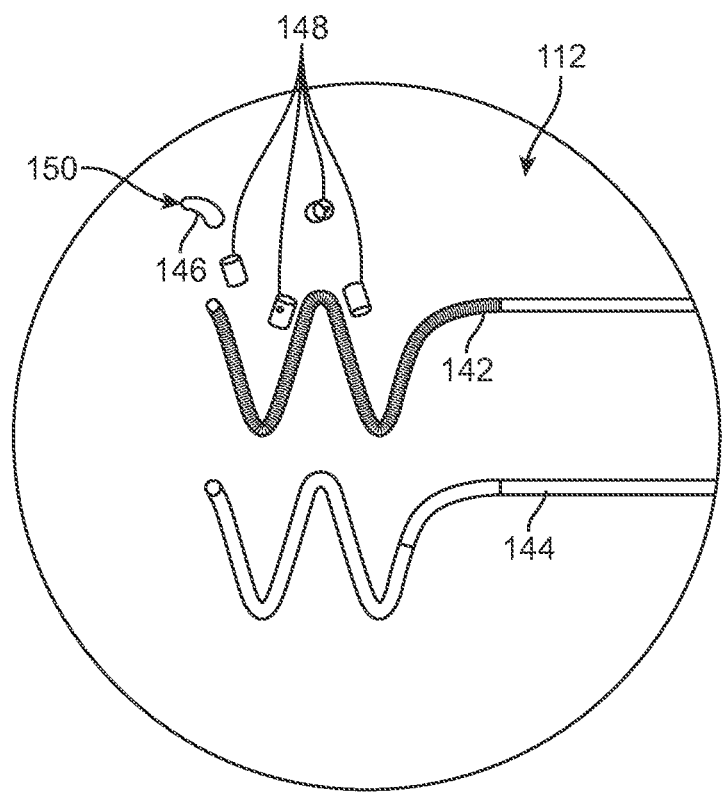

FIG. 2 is an exploded profile view of the catheter 102. FIGS. 3, 4 and 6 are enlarged exploded profile views of portions of the catheter 102 taken at respective locations designated in FIG. 2. With reference to FIGS. 2-4 and 6 together, the handle 110 can include mating shell segments 120 (individually identified as shell segments 120a, 120b) and a connector 122 (e.g., a luer connector) operably positioned between the mating shell segments 120. The handle 110 can further include a distally tapered strain-relief element 124 operably connected to distal ends of the shell segments 120. Slidably positioned over the shaft 108, the catheter 102 can include a loading tool 126 configured to facilitate loading the catheter 102 onto a guide wire (not shown). When assembled, the shaft 108 can extend through coaxial lumens (also not shown) of the strain-relief element 124 and the loading tool 126, respectively, and between the shell segments 120 to the connector 122.

The shaft 108 can include an assembly of parallel tubular segments. At its proximal end portion 108a and extending distally though a majority of its intermediate portion 108c, the shaft 108 can include a proximal hypotube segment 128, a proximal jacket 130, a first electrically insulative tube 132, and a guide-wire tube 134. The first electrically insulative tube 132 and the guide-wire tube 134 can be disposed side-by-side within the proximal hypotube segment 128. The first electrically insulative tube 132 can be configured to carry electrical leads (not shown) and to electrically insulate the electrical leads from the proximal hypotube segment 128. The guide-wire tube 134 can be configured to carry a guide wire (not shown). The proximal jacket 130 can be disposed around at least a portion of an outer surface of the proximal hypotube segment 128. The proximal hypotube segment 128 can include a proximal stem 136 at its proximal end and a distal skive 138 at its distal end. The proximal jacket 130 and the proximal hypotube segment 128 are discussed in greater detail below with reference to FIGS. 7-9.

With reference again to FIGS. 2-4 and 6, the first electrically insulative tube 132 and the guide-wire tube 134 can extend distally beyond the distal skive 138. The shaft 108 can include an intermediate tube 140 beginning proximally at a region of the shaft 108 at which the first electrically insulative tube 132 and the guide-wire tube 134 distally emerge from the proximal hypotube segment 128. The intermediate tube 140 can be more flexible than the proximal hypotube segment 128. At the region of the shaft 108 at which the first electrically insulative tube 132 and the guide-wire tube 134 distally emerge from the proximal hypotube segment 128, the intermediate tube 140 can be coaxially aligned with the proximal hypotube segment 128 so as to receive the first electrically insulative tube 132 and the guide-wire tube 134. From this region, the intermediate tube 140 can extend distally to the distal end portion 108b of the shaft 108. The first electrically insulative tube 132 can distally terminate within the intermediate tube 140. In contrast, the guide-wire tube 134 can extend through the entire length of the intermediate tube 140. At a distal end of the intermediate tube 140, the shaft 108 can be operably connected to the neuromodulation element 112.

Figure 5:
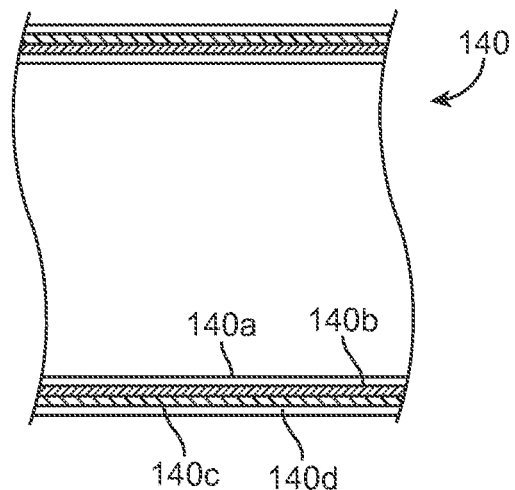
FIG. 5 is a further enlarged cross-sectional view of an intermediate tube of the shaft shown in FIG. 1 taken along a line 5-5 designated in FIG. 4.

FIG. 5 is a further enlarged cross-sectional view of the intermediate tube 140 taken along a line 5-5 designated in FIG. 4. Arranged from innermost to outermost, the intermediate tube 140 can include an inner polymer layer 140a, a metal braid 140b, a first outer polymer layer 140c, and a second outer polymer layer 140d. In a particular embodiment, the inner polymer layer 140a is made of polyimide (e.g., about 0.006 inch thick); the metal braid 140b is made of stainless steel; the first outer polymer layer 140c is made of coated polyimide (e.g., three coats); and the second outer polymer layer 140d is made of polyether block amide (e.g., PEBAX®) (e.g., about 0.00125 inch thick). Other suitable compositions and arrangements are also possible. In some embodiments, at least a portion of the intermediate tube 140 is film-cast. For example, disposing the first outer polymer layer 140c onto the metal braid 140b as a series of thin films can allow the thickness of the first outer polymer layer 140c to be precisely controlled. Accordingly, the first outer polymer layer 140c can be just thick enough to prevent the ends of the metal braid 140b from becoming exposed or otherwise damaged when thermally bonding the intermediate tube 140 to the proximal and distal hypotube segments 128, 142, respectively, but not so thick as to cause the intermediate tube 140 to become excessively stiff. This can reduce or eliminate the need to locally reinforce the ends of the intermediate tube 140 or to splice coupling components onto the ends of the intermediate tube 140 to facilitate bonding the intermediate tube 140 to the proximal and distal hypotube segments 128, 142.

The neuromodulation element 112 can include a distal hypotube segment 142 coupled to the distal end of the intermediate tube 140. The neuromodulation element 112 can also include a distal jacket 144 disposed around at least a portion of an outer surface of the distal hypotube segment 142. As shown, the neuromodulation element 112 can further include band electrodes 146 disposed outside the distal jacket 144 at spaced-apart positions along a longitudinal axis of the distal jacket 144. At a distal end of the distal hypotube segment 142, the neuromodulation element 112 can include a distally tapering atraumatic tip 148. The guide-wire tube 134 can extend through the distal hypotube segment 142 to a distal opening 150 of the tip 148. The electrical leads can respectively extend through the distal hypotube segment 142 to the band electrodes 146.

In FIGS. 2 and 6, the neuromodulation element 112 is shown in a radially expanded deployed state. The neuromodulation element 112 can be movable from a low-profile delivery state to the radially expanded deployed state. When the neuromodulation element 112 is in the radially expanded deployed state, the distal hypotube segment 142 can have a shape that is more helical (spiral) than its shape when the neuromodulation element 112 is in the low-profile delivery state. In at least some cases, the distal hypotube segment 142 has the more helical shape when at rest and is configured to be forced into the less helical shape by an external sheath (not shown). The distal hypotube segment 142 can be made at least partially of nitinol, stainless steel, or another suitable material well suited for resiliently moving between the more helical and less helical shapes. In at least some cases, the material of the distal hypotube segment 142 is electrically conductive. Accordingly, the neuromodulation element 112 can include a second electrically insulative tube 152 disposed around an outer surface of the distal hypotube segment 142 so as to electrically separate the band electrodes 146 from the distal hypotube segment 142. In some embodiments, the first and second electrically insulative tubes 132, 152 are made at least partially (e.g., predominantly or entirely) of polyimide and polyether block amide, respectively. In other embodiments, the first and second electrically insulative tubes 132, 152 can be made of other suitable materials.

Figure 7:
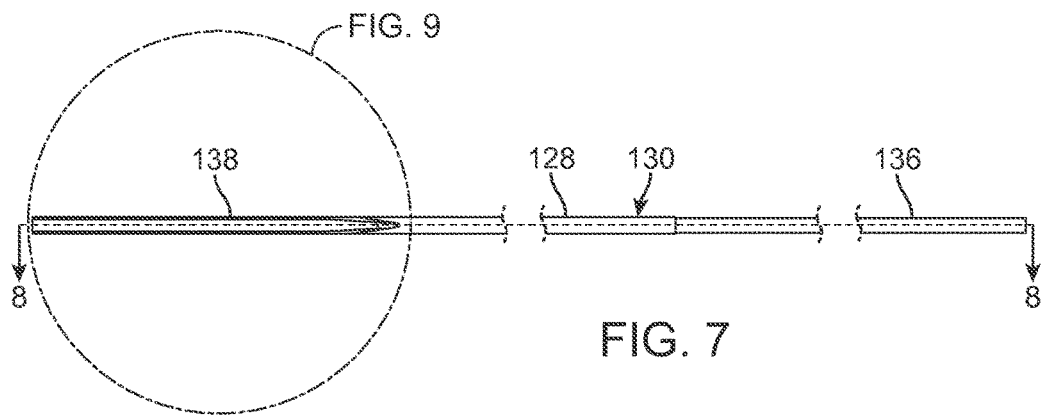
FIG. 7 is a profile view of a proximal hypotube segment and a proximal jacket of the shaft shown in FIG. 1.
Figure 8:
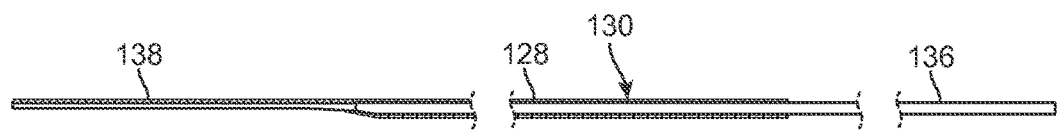
FIG. 8 is a cross-sectional profile view of the proximal hypotube segment and the proximal jacket shown in FIG. 7 taken along a line 8-8 designated in FIG. 7.
Figure 9:
FIG. 9 is an enlarged profile view of a portion of the proximal hypotube segment and the proximal jacket shown in FIG. 7 taken at a location designated in FIG. 7.

FIG. 7 is a profile view of the proximal hypotube segment 128 and the proximal jacket 130. FIG. 8 is a cross-sectional profile view of the proximal hypotube segment 128 and the proximal jacket 130 taken along a line 8-8 designated in FIG. 7. FIG. 9 is an enlarged profile view of a portion of the proximal hypotube segment 128 and the proximal jacket 130 taken at a location designated in FIG. 7. As shown in FIGS. 7 and 8, the proximal jacket 130 can be absent from the outer surface of the proximal hypotube segment 128 at the proximal stem 136. This can be useful, for example, to facilitate connecting the proximal hypotube segment 128 to the connector 122. In contrast, the proximal jacket 130 can be disposed on at least a portion of the outer surface of the proximal hypotube segment 128 at the distal skive 138. In some embodiments, the proximal hypotube segment 128 is made at least partially (e.g., predominantly or entirely) of nitinol. In these and other embodiments, the proximal jacket 130 can be made at least partially (e.g., predominantly or entirely) of a polymer blend including polyether block amide and polysiloxane. For example, the polymer blend can include greater than 15% polysiloxane. In a particular embodiment, the polymer blend includes about 20% by weight polyether block amide and about 80% by weight polyether block amide. This material may allow the proximal jacket 130 to have sufficient lubricity for use without an outer coating, among other potential advantages. In still other embodiments, the proximal hypotube segment 128 and the proximal jacket 130 can be made of other suitable materials.

Figure 10:
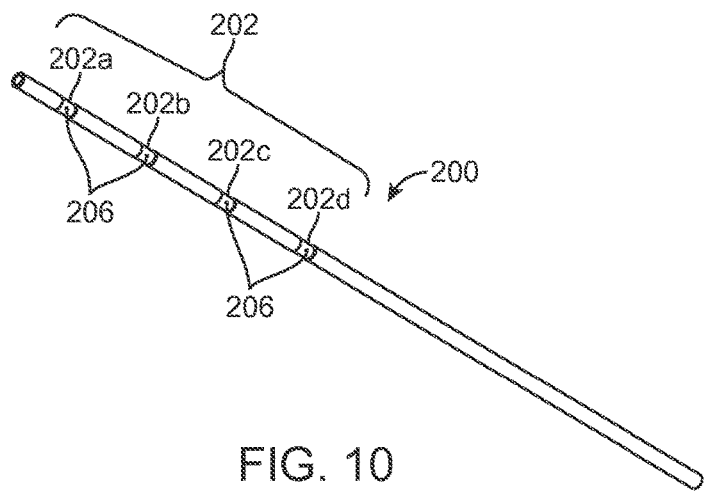
FIG. 10 is a perspective view of a distal jacket of a neuromodulation element of a neuromodulation catheter configured in accordance with an embodiment of the present technology. The distal jacket is shown in FIG. 10 including reduced-diameter segments.
Figure 11:
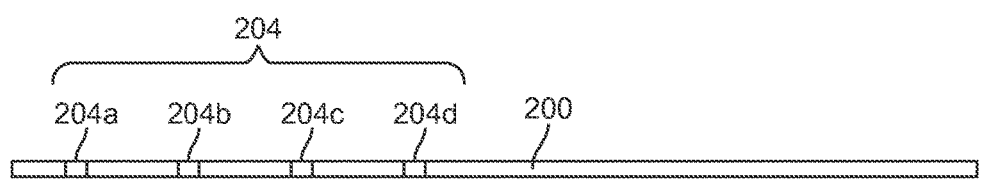
FIG. 11 is a profile view of the distal jacket shown in FIG. 10 and band electrodes respectively seated in the reduced-diameter segments.
Figure 12:
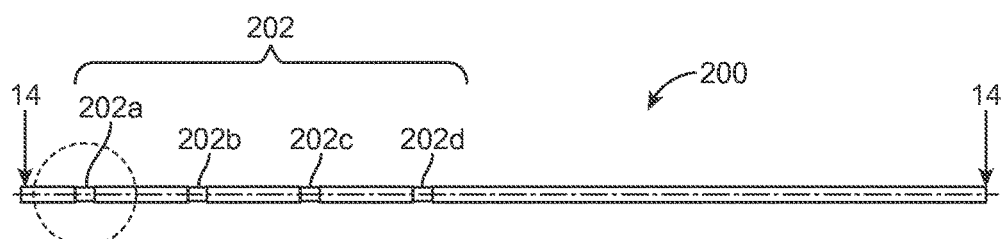
FIG. 12 is a profile view of the distal jacket shown in FIG. 10.
Figure 13:
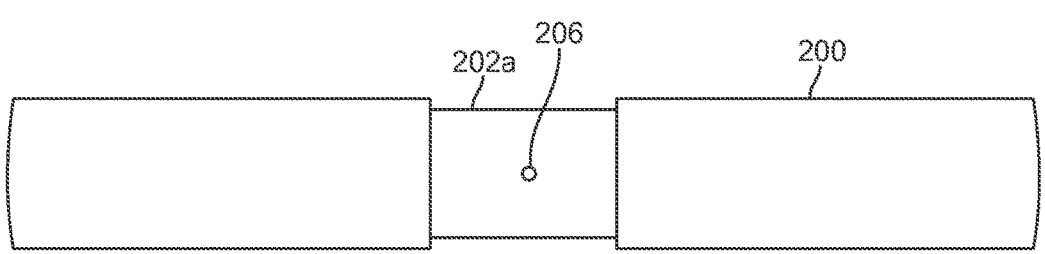
FIG. 13 is an enlarged profile view of a portion of the distal jacket shown in FIG. 9 taken at a location designated in FIG. 12.
Figure 14:
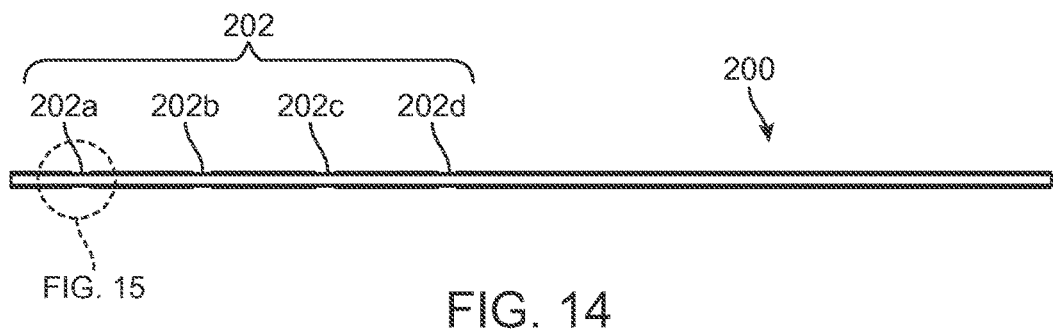
FIG. 14 is a cross-sectional profile view of the distal jacket shown in FIG. 10 taken along a line 14-14 designated in FIG. 12.

FIG. 10 is a perspective view of a distal jacket 200 of a neuromodulation element of a neuromodulation catheter configured in accordance with an embodiment of the present technology. The distal jacket 200, for example, can be used in the neuromodulation element 112 (FIGS. 1, 2 and 6) in place of the distal jacket 144 (FIGS. 2 and 6). Accordingly, the distal jacket 200 may be described below in conjunction with components of the catheter 102 (FIGS. 1 and 2). The distal jacket 200 can include reduced-diameter segments 202 (individually identified as reduced-diameter segments 202a-202d) extending through its outer surface. FIG. 11 is a profile view of the distal jacket 200 and band electrodes 204 (individually identified as band electrodes 204a-204d) respectively seated in the reduced-diameter segments 202. FIG. 12 is a profile view of the distal jacket 200 without the band electrodes 204. FIG. 13 is an enlarged profile view of a portion of the distal jacket 200 taken at a location designated in FIG. 12. FIG. 14 is a cross-sectional profile view of the distal jacket 200 taken along a line 14-14 designated in FIG. 12.

With reference to FIGS. 10-14 together, the distal jacket 200 can be tubular and configured to be disposed around at least a portion of an outer surface of the distal hypotube segment 142 (FIGS. 2 and 6). The reduced-diameter segments 202 can be insets, pockets, grooves, or other suitable features configured to respectively seat the band electrodes 204. In the illustrated embodiment, the distal jacket 200 includes exactly four reduced-diameter segments 202 spaced apart along its longitudinal axis. Alternatively, the distal jacket 200 can include exactly one, two, three, five, six or a greater number of reduced-diameter segments 202. The reduced-diameter segments 202 may be spaced apart at equal distances or at different distances. The distal jacket 200 can include openings 206 respectively positioned at the reduced-diameter segments 202. A neuromodulation catheter including the distal jacket 200 can include electrical leads (not shown) extending from respective reduced-diameter segments 202, through respective openings 206, through a lumen of the distal hypotube segment 142 (FIGS. 2 and 6), through the intermediate tube 140, and through the proximal hypotube segment 128 to the handle 110. In this way, the electrical leads can respectfully connect the band electrodes 204 to proximal components of a neuromodulation catheter including the distal jacket 200.

Figure 15:
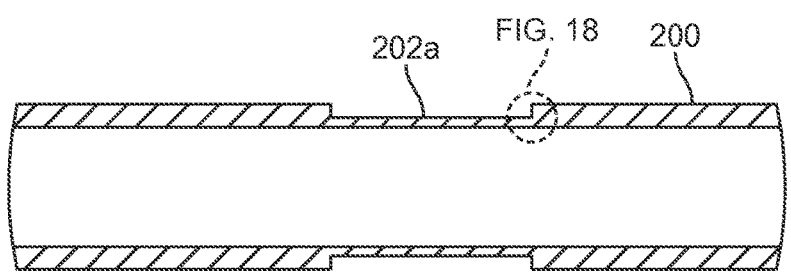
FIGS. 15-17 are enlarged cross-sectional profile views of a portion of the distal jacket shown in FIG. 10 at a location designated in FIG. 14. The portion of the distal jacket shown in FIGS. 15-17 includes one of the reduced-diameter segments shown in FIG. 10.
Figure 16:
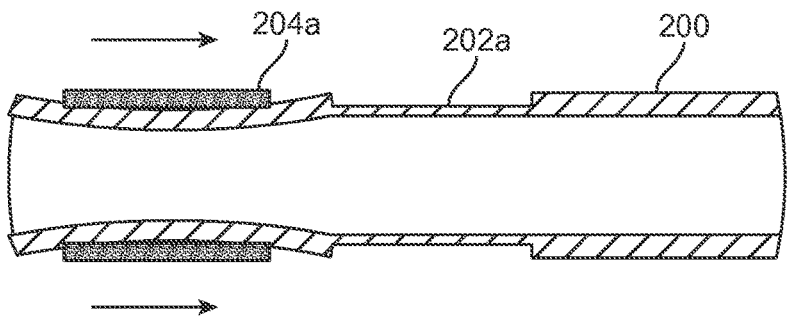
Figure 17:
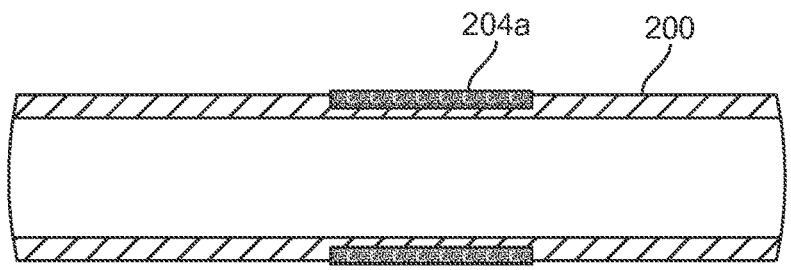

FIGS. 15-17 are enlarged cross-sectional profile views of a portion of the distal jacket 200 at a location designated in FIG. 14. At this location, the distal jacket 200 can include the reduced-diameter segment 202a. In FIG. 15, the portion of the distal jacket 200 is shown without the band electrode 204a corresponding to the reduced-diameter segment 202a. In FIG. 16, the portion of the distal jacket 200 is shown resiliently deformed inwardly as the band electrode 204a is moved toward the reduced-diameter segment 202a. In FIG. 17, the portion of the distal jacket 200 is shown with the band electrode 204a seated in the reduced-diameter segment 202a. With reference to FIGS. 10-17 together, the band electrodes 204 can respectively form closed loops extending circumferentially around the distal jacket 200. In at least some cases, a minimum inner diameter of the band electrodes 204 is smaller than a maximum outer diameter of distal jacket 200 between the reduced-diameter segments 202. To facilitate assembly, the distal jacket 200 between the reduced-diameter segments 202 can be resilient in response to peristaltic deflection of a magnitude corresponding to a difference between the maximum outer diameter of the distal jacket 200 between the reduced-diameter segments 202 and the minimum inner diameter of the band electrodes 204. Suitable materials for the distal jacket 200 include polymer blends including polyurethane and polysiloxane, among others.

A maximum outer diameter of the band electrodes 204 and the maximum outer diameter of the distal jacket 200 between the reduced-diameter segments 202 can be at least generally equal (e.g., within 5%, 3%, or 2% of one another). Thus, once the band electrodes 204 are respectively seated in the reduced-diameter segments 202, outer surfaces of the band electrodes 204 and the distal jacket 200 between the reduced-diameter segments 202 can be at least generally flush. This can be useful, for example, to reduce or eliminate potentially problematic ridges (e.g., circumferential steps) at distal and proximal ends of the individual band electrodes 204. This, in turn, can reduce or eliminate the need for fillets (e.g., adhesive fillets, such as glue fillets) at the distal and proximal ends of the individual band electrodes 204. In at least some embodiments, the distal jacket 200 and the band electrodes 204 can be bonded to one another without any exposed adhesive. For example, an adhesive (not shown) can be disposed between the band electrodes 204 and the distal jacket 200 at the reduced-diameter segments 202.

Figure 18:
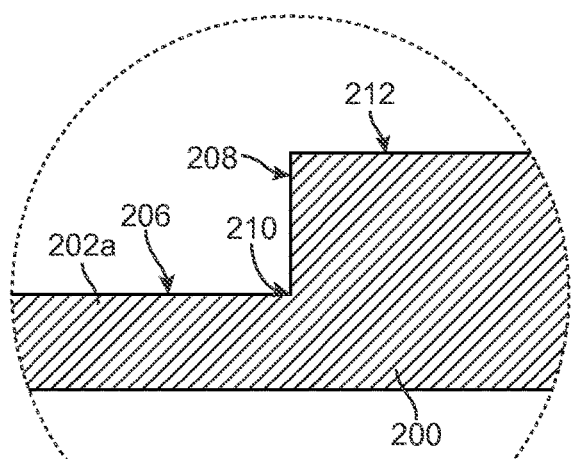
FIG. 18 is an enlarged cross-sectional profile view of a sidewall of one of the reduced-diameter segments shown in FIG. 10 at a location designated in FIG. 15.

FIG. 18 is an enlarged cross-sectional profile view of a sidewall of the reduced-diameter segment 202a at a location designated in FIG. 15. As shown in FIG. 18, the reduced-diameter segment 202a can include a floor 206, a sidewall 208, and a corner 210 therebetween. The distal jacket 200 can further include a rim 212 bordering the reduced-diameter segment 202a. In the illustrated embodiment, the sidewall 208 is vertical and perpendicular to the floor 206 and the rim 212. In particular, the sidewall 208 meets the floor 206 and the rim 212 at a 90° angle and a 270° angle, respectively. This configuration of the sidewall 208 can facilitate secure seating of a band electrode (not shown in FIG. 18) in the reduced-diameter segment 202a without a gap being formed between the band electrode and an upper portion of the sidewall 208. Such a gap can be problematic, for example, because it can present an edge that may interfere with smooth movement of the distal jacket 200 through a patient's vasculature. Disadvantageously, tensile loading on the distal jacket 200 may tend to concentrate at the corner 210. This can adversely affect the durability of the distal jacket 200.

Figure 19:
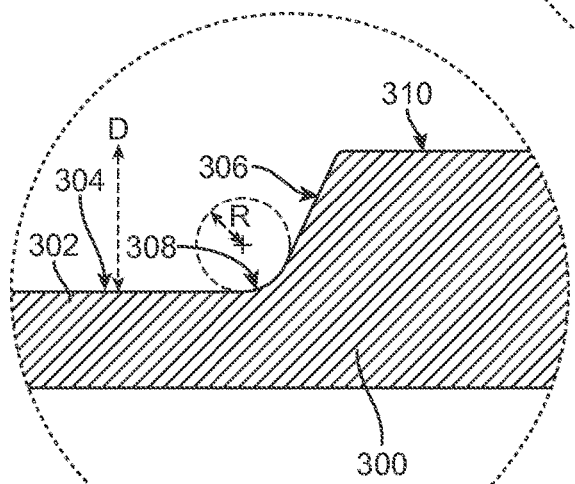
FIGS. 19 and 20 are enlarged cross-sectional profile views of sidewalls of reduced-diameter segments having configurations different than the configuration of the sidewall shown in FIG. 18.
Figure 20:
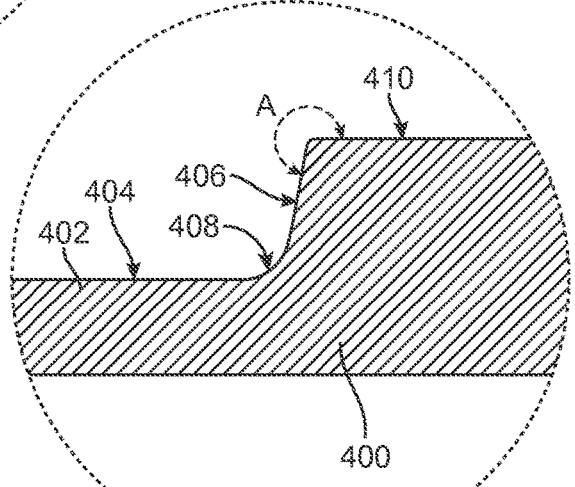

Sidewall configurations different than the configuration shown in FIG. 18 may be advantageous in at least some cases. FIGS. 19 and 20 illustrate two examples of such alternative configurations. FIG. 19, in particular, is an enlarged cross-sectional profile view of a portion of a distal jacket 300 including a reduced-diameter segment 302 having a floor 304, a sidewall 306, and a rounded junction 308 therebetween. The distal jacket 300 can further include a rim 310 bordering the reduced-diameter segment 302. In the illustrated embodiment, the sidewall 306 is slanted relative to the floor 304 and the rim 310. The reduced-diameter segment 302 can have a depth (D) between the floor 304 and the rim 310. The rounded junction 308 can have a radius (R) within a range from 25% to 50% of the depth. In at least some embodiments, the radius is within a range from 0.5 mil to 3 mils (e.g., a range from 1 mil to 2 mils). The shape of the rounded junction 308 can promote diffusion of tensile loading on the distal jacket 300, thereby enhancing the durability of the distal jacket 300. Furthermore, the sidewall 306 and the rounded junction 308 can be entirely on one side of a plane along which a portion of the floor 304 directly adjacent to the rounded junction 308 lies. Because the sidewall 306 and the rounded junction 308 do not extend through this plane, the material thickness of the distal jacket 300 at the rounded junction 308 can be no less than the material thickness of the distal jacket 300 elsewhere along the reduced-diameter segment 302. Correspondingly, the tensile strength of the distal jacket 300 at the rounded junction 308 can be no less than the material thickness of the distal jacket 300 elsewhere along the reduced-diameter segment 302.

FIG. 20 is an enlarged cross-sectional profile view of a portion of a distal jacket 400 including a reduced-diameter segment 402 having a floor 404, a sidewall 406, and a rounded junction 408 therebetween. The distal jacket 400 can further include a rim 410 bordering the reduced-diameter segment 402. In the illustrated embodiment, the sidewall 406 is more vertical relative to the floor 404 and the rim 410 than the sidewall 306 of the reduced-diameter segment 302 shown in FIG. 19. In at least some embodiments, the sidewall 406 from the rounded junction 408 to the rim 410 has an average angle (A) greater than 240° (e.g., greater than 260°) relative to the rim 410. As discussed above with reference to FIG. 18, vertical or near-vertical orientation of the sidewall 406 can facilitate secure seating of a band electrode (not shown in FIG. 20) in the reduced-diameter segment 402 without a gap or with only a minor gap being formed between the band electrode and an upper portion of the sidewall 406.

Selected Examples of Manufacturing Methods for Neuromodulation Elements

Figure 21:
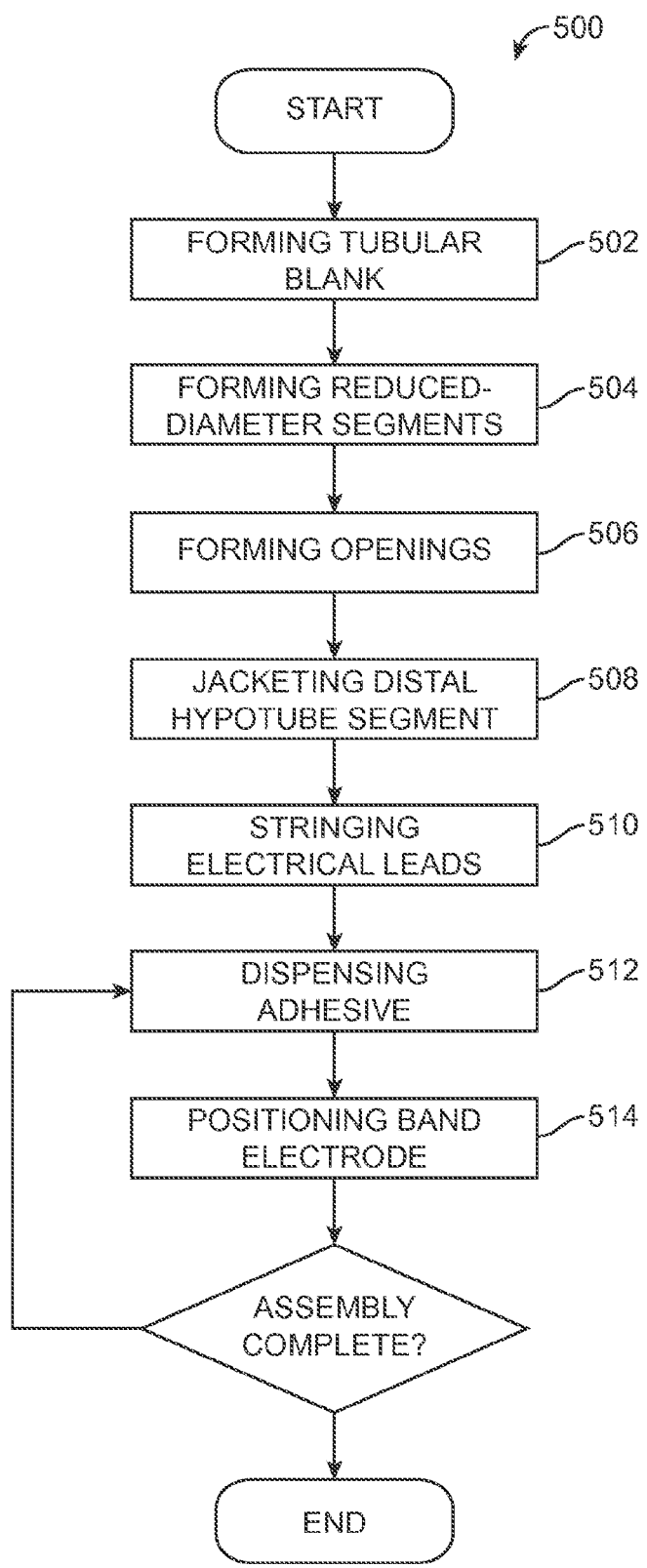
FIG. 21 is a flow chart illustrating a method for making a neuromodulation element including the distal jacket shown in FIG. 10 and the band electrodes shown in FIG. 11 in accordance with an embodiment of the present technology.

FIG. 21 is a flow chart illustrating a method 500 for making a neuromodulation element including the distal jacket 200 and the band electrodes 204 in accordance with an embodiment of the present technology. With reference to FIGS. 10-21 together, the method 500 can begin with forming the distal jacket 200. This can include forming a tubular blank (block 502) (e.g., by extrusion) and then using a subtractive process (e.g., by laser ablation) to remove portions of the blank and thereby form the reduced-diameter segments 202 (block 504). The same or a different subtractive process can be used to form the openings 206 (block 506). Alternatively, the distal jacket 200 can be formed by injection molding or another suitable technique that allows the reduced-diameter segments 202 and/or the openings 206 to be formed without the need for a subtractive process. When a subtractive process is used to form the reduced-diameter segments 202, the subtractive process can be precisely controlled so as to leave an innermost portion of a wall of the distal jacket 200 intact at the reduced-diameter segments 202. Laser ablation is one example of a suitable subtractive process for forming the reduced-diameter segments 202. Laser ablation can include loading the blank onto a mandrel and then rotating the blank and the mandrel relative to an ablative laser (or rotating the ablative laser relative to the black and the mandrel) under computerized control. The mandrel can conductively cool the innermost portion of the wall of the distal jacket 200 so as to prevent this portion of the wall from reaching ablative temperatures at the reduced-diameter segments 202. Furthermore, laser ablation and other subtractive processes can be carefully controlled to avoid forming a notch or other indentation in the distal jacket 200 below the floor 206 at the corner 210. When present, such an indentation may unduly decrease the tensile strength of the distal jacket 200. Other techniques for forming the reduced-diameter segments 202 are also possible.

The method 500 can further include jacketing the distal hypotube segment 142 (block 508), such as by positioning the distal jacket 200 and the distal hypotube segment 142 relative to one another so that the distal jacket 200 is disposed around at least a portion of an outer surface of the distal hypotube segment 142. In at least some embodiments, the form and/or other aspects of the distal jacket 200 may allow the distal jacket 200 to be disposed around at least a portion of the outer surface of the distal hypotube segment 142 without swaging the distal jacket 200. When the distal hypotube segment 142 is positioned within the distal jacket 200, the method 500 can include respectively stringing electrical leads (block 510) from the reduced-diameter segments 202 through a lumen of the distal hypotube segment 142. Next, the method 500 can include dispensing an adhesive (block 512) onto the distal jacket 200 at the reduced-diameter segment 202*d*. Then, the method 500 can include positioning the band electrode 204*d* (block 514) at the reduced-diameter segment 202*d*. As discussed above with reference to FIGS. 15-17, positioning the band electrode 204*d* can include resiliently deforming the distal jacket 200 inwardly while passing (e.g., advancing or threading) the distal jacket 200 through a channel of the band electrode 204*d* so as to move the band electrode 204*d* toward a longitudinal position at which the band electrode 204*d* is aligned with the reduced-diameter segment 202*d*. The same process can be used to install the band electrodes 204*c*, the band electrode 204*b*, and finally the band electrode 204*a*.

Renal Neuromodulation

Catheters configured in accordance with at least some embodiments of the present technology can be well suited (e.g., with respect to sizing, flexibility, operational characteristics, and/or other attributes) for performing renal neuromodulation in human patients. Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, or induced in another suitable manner or combination of manners at one or more suitable treatment locations during a treatment procedure. The treatment location can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery. Various suitable modifications can be made to the catheters described above to accommodate different treatment modalities. For example, the band electrodes 204 (FIG. 11) can be replaced with transducers to facilitate transducer-based treatment modalities.

Renal neuromodulation can include an electrode-based or treatment modality alone or in combination with another treatment modality. Electrode-based or transducer-based treatment can include delivering electricity and/or another form of energy to tissue at or near a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at or near a treatment location. For example, neuromodulation in accordance with embodiments of the present technology can include delivering RF energy, pulsed electrical energy, microwave energy, optical energy, focused ultrasound energy (e.g., high-intensity focused ultrasound energy), and/or another suitable type of energy. An electrode or transducer used to deliver this energy can be used alone or with other electrodes or transducers in a multi-electrode or multi-transducer array.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular or intraluminal), optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array, which can be curved or straight.

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of luminal structures that perfuse the target neural fibers. In cases where luminal structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of luminal structures that perfuse the target fibers. In some patients, it can be desirable to heat tissue to temperatures that are sufficient to ablate the target neural fibers or the luminal structures, but that are less than about 90° C. (e.g., less than about 85° C., less than about 80° C., or less than about 75° C.).

Conclusion

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments may also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

The methods disclosed herein include and encompass, in addition to methods of practicing the present technology (e.g., methods of making and using the disclosed devices and systems), methods of instructing others to practice the present technology. For example, a method in accordance with a particular embodiment includes forming a tubular jacket, resiliently deforming the jacket inwardly while passing the jacket through a channel of a band electrode, and positioning the jacket and a hypotube segment relative to one another so that the jacket is disposed around at least a portion of an outer surface of the hypotube segment. A method in accordance with another embodiment includes instructing such a method.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments of the present technology.

We claim:

1. A neuromodulation catheter, comprising:
   an elongate shaft; and
   a neuromodulation element operably connected to the shaft via a distal end portion of the shaft, the neuromodulation element being movable from a low-profile delivery state to a radially expanded deployed state, the neuromodulation element including:
      a hypotube segment configured to have a first shape when the neuromodulation element is in the delivery state and a second shape when the neuromodulation element is in the deployed state, the second shape being more helical than the first;
a tubular jacket disposed around at least a portion of an outer surface of the hypotube segment, an outer surface of the jacket defining reduced-diameter segments spaced apart along its longitudinal; and
band electrodes respectively seated in the reduced-diameter segments and respectively forming closed loops extending circumferentially around the jacket, wherein a minimum inner diameter of the band electrodes is smaller than a maximum outer diameter of jacket between the reduced-diameter segments.

2. The neuromodulation catheter of claim 1 wherein the jacket between the reduced-diameter segments is resilient in response to peristaltic deflection of a magnitude corresponding to a difference between the maximum outer diameter of the jacket between the reduced-diameter segments and the minimum inner diameter of the band electrodes.

3. The neuromodulation catheter of claim 1, further comprising adhesive disposed between the band electrodes and the jacket at the reduced-diameter segments.

4. The neuromodulation catheter of claim 1 wherein the reduced-diameter segments are fully circumferential.

5. The neuromodulation catheter of claim 1 wherein:
the jacket includes openings respectively positioned at the reduced-diameter segments;
the neuromodulation catheter further comprises electrical leads respectively connected to the band electrodes; and
the electrical leads respectively extend through the openings.

6. The neuromodulation catheter of claim 1 wherein a maximum outer diameter of the band electrodes and the maximum outer diameter of the jacket between the reduced-diameter segments are at least generally equal.

7. The neuromodulation catheter of claim 1 wherein at least one of the reduced-diameter segments has a side wall, a floor, and a rounded junction therebetween.

8. The neuromodulation catheter of claim 7 wherein:
a portion of the floor directly adjacent to the rounded junction lies along a plane; and
the wall and the rounded junction do not extend through the plane.

9. The neuromodulation catheter of claim 8 wherein:
the jacket includes a rim bordering a respective reduced-diameter segment of the at least one reduced-diameter segment;
the respective reduced-diameter segment has a depth between the floor and the rim; and
the rounded junction has a radius within a range from 35% to 50% of the depth.

10. The neuromodulation catheter of claim 8 wherein:
the jacket includes a rim bordering a respective reduced-diameter segment of the at least one reduced-diameter segment;
the respective reduced-diameter segment has depth between the floor and the rim; and
the rounded junction has a radius within a range from 0.5 mil to 3 mils.

11. The neuromodulation catheter of claim 8 wherein:
the jacket includes a rim bordering a respective reduced-diameter segment of the at least one reduced-diameter segment; and
the sidewall from the junction to the rim has an average angle greater than 240° relative to the rim.

12. The neuromodulation catheter of claim 8 wherein:
the jacket includes a rim bordering a respective reduced-diameter segment of the at least one reduced-diameter segment; and
the sidewall from the junction to the rim has an average angle greater than 260° relative to the rim.

13. The neuromodulation catheter of claim 1 wherein the jacket is made at least partially of a polymer blend including polyurethane and polysiloxane.

14. The neuromodulation catheter of claim 1, wherein the jacket is made at least partially of a polymer blend including polyether block amide and polysiloxane.

15. The neuromodulation catheter of claim 14 wherein the jacket includes polysiloxane at greater than 15% by weight.

16. The neuromodulation catheter of claim 14 wherein the jacket includes polysiloxane at about 20% by weight.

17. The neuromodulation catheter of claim 14 wherein the jacket includes polyether block amide at about 80% by weight.

18. The neuromodulation catheter of claim 1 wherein the hypotube segment is made at least partially of nitinol.

19. The neuromodulation catheter of claim 1 wherein:
the hypotube segment includes a proximal stem; and
the jacket is not disposed around the outer surface of the hypotube segment at the proximal stem.

20. The neuromodulation catheter of claim 1 wherein the jacket is uncoated.

21. The neuromodulation catheter of claim 1 wherein:
the hypotube segment includes a distal skive; and
the jacket is disposed on at least a portion of the outer surface of the hypotube segment at the distal skive.

22. A method comprising forming a neuromodulation element, wherein forming the neuromodulation element comprises:
forming a tubular jacket, an outer surface of the jacket defining reduced-diameter segments spaced apart along its longitudinal axis;
positioning a band electrode in a reduced-diameter segment of the reduced diameter segments, the band electrode forming a closed loop extending circumferentially around the jacket, wherein a minimum inner diameter of the band electrode is smaller than a maximum outer diameter of jacket between the reduced-diameter segments; and
positioning the jacket and a hypotube segment relative to one another so that the jacket is disposed around at least a portion of an outer surface of the hypotube segment, wherein the hypotube segment is configured to have a first shape in a delivery state of the neuromodulation element and a second shape in a deployed state of the neuromodulation element, the second shape being more helical than the first shape.

23. The method of claim 22, wherein the reduced-diameter segments include a first reduced-diameter segment and a second reduced-diameter segment, wherein positioning the band electrode in the reduced-diameter segment comprises positioning a first band electrode in the first reduced-diameter segment, the method further comprising positioning a second band electrode in the second reduced-diameter segment.

24. The method of claim 22 wherein the method does not include swaging the jacket after forming the jacket and before positioning the jacket and the hypotube segment relative to one another.

25. The method of claim 22 wherein forming the jacket includes forming the jacket by injection molding.

26. The method of claim 22 wherein forming the jacket includes:
   forming a tubular blank by extrusion; and
   removing a portion of the blank to form the reduced-diameter segments.

27. The method of claim 22 wherein removing the portion of the blank includes removing the portion of the blank by laser ablation.

\* \* \* \* \*